(12) United States Patent
Barney et al.

(10) Patent No.: US 7,261,102 B2
(45) Date of Patent: Aug. 28, 2007

(54) BREATH-ENHANCED ULTRASONIC NEBULIZER AND DEDICATED UNIT DOSE AMPOULE

(75) Inventors: Brian Barney, Essex (GB); Sophia Chew, London (GB); Paul Fairburn, Hertfordshire (GB); David O'Leary, Essex (GB); Rachel Striebig, London (GB)

(73) Assignee: Norton Healthcare Ltd. (GB)

( * ) Notice: Subject to any disclaimer, the term of this patent is extended or adjusted under 35 U.S.C. 154(b) by 0 days.

(21) Appl. No.: 10/487,611

(22) PCT Filed: Aug. 30, 2002

(86) PCT No.: PCT/US02/27712

§ 371 (c)(1),
(2), (4) Date: Nov. 29, 2004

(87) PCT Pub. No.: WO03/026556

PCT Pub. Date: Apr. 3, 2003

(65) Prior Publication Data

US 2005/0081845 A1     Apr. 21, 2005

Related U.S. Application Data

(60) Provisional application No. 60/318,737, filed on Sep. 12, 2001, provisional application No. 60/318,698, filed on Sep. 12, 2001.

(51) Int. Cl.
*A61M 11/00*     (2006.01)
(52) U.S. Cl. .............................. 128/200.14; 128/200.21
(58) Field of Classification Search ........... 128/200.11, 128/200.14, 200.16, 200.17, 200.18, 200.21, 128/203.12, 203.13, 203.14, 203.16, 203.17, 128/203.26, 203.27, 204.13, 204.14, 203.24
See application file for complete search history.

(56) References Cited

U.S. PATENT DOCUMENTS

| | | | | |
|---|---|---|---|---|
| 4,832,012 A | * | 5/1989 | Raabe et al. ............ | 128/200.21 |
| 5,163,617 A | * | 11/1992 | Clifford et al. .......... | 239/102.2 |
| 5,170,782 A | | 12/1992 | Kocinski | |
| 5,301,663 A | * | 4/1994 | Small, Jr. .............. | 128/200.18 |
| 5,388,571 A | * | 2/1995 | Roberts et al. ......... | 128/203.12 |
| 5,551,416 A | * | 9/1996 | Stimpson et al. ...... | 128/200.16 |
| 6,161,536 A | | 12/2000 | Redmon et al. | |
| 6,283,118 B1 | * | 9/2001 | Lu ......................... | 128/200.16 |
| 6,450,163 B1 | * | 9/2002 | Blacker et al. ........ | 128/200.18 |
| 6,513,519 B2 | | 2/2003 | Gallem | |
| 6,631,721 B1 | * | 10/2003 | Salter et al. ........... | 128/207.14 |
| 6,640,804 B2 | * | 11/2003 | Ivri et al. .............. | 128/200.16 |
| 6,732,731 B1 | * | 5/2004 | Tseng .................... | 128/200.21 |
| 2002/0134377 A1 | * | 9/2002 | Loeffler et al. ........ | 128/200.24 |

\* cited by examiner

*Primary Examiner*—Teena Mitchell
(74) *Attorney, Agent, or Firm*—Lerner, David, Littenberg, Krumholz & Mentlik, LLP

(57) ABSTRACT

A medicament delivery system comprises a nebulizer device, an open-faced mist chamber-defining element having a tubular input/output port, a tubular inhalation port connecting to the output port of the mist chamber-defining element, and a sealed unit dose ampoule adapted to fit within the mist chamber-defining element. The nebulizer device includes an ultrasonic transducer responsive to applied electrical energy to generate ultrasonic energy, an ultrasonic transmission horn between an input energy surface at an input end and an energy delivery surface at an output end. The sealed unit dose ampoule can be placed directly into the nebulizer device and acts as both the dose cup and baffle, so that the chance of spillage of drug and the number of components to be cleaned are minimized.

14 Claims, 8 Drawing Sheets

BREATH-ENHANCED ULTRASONIC NEBULIZER AND DEDICATED UNIT DOSE AMPOULE

CROSS-REFERENCE TO RELATED APPLICATIONS

This application is a national stage entry under 35 U.S.C. § 371 of international Application PCT/US02/27712, filed Aug. 30, 2002, which claims the benefit under § 119e of the filing dates of U.S. Provisional Application 60/318,737 and 60/318,698, both of which were filed on Sep. 12, 2001.

FIELD OF THE INVENTION

The invention relates to an apparatus and method for administering medicament for inhalation by a patient. More particularly, the present invention relates to a nebulizer having a unit dose ampoule and a valve arrangement for use in a nebulizer medicament delivery system.

BACKGROUND OF THE INVENTION

Nebulizers are well known for dispensing medicament to the lungs of a patient for treating asthma, for example. A typical prior art nebulizer assembly for such therapeutic purposes includes a nebulizer which contains an electrically driven ultrasonic energy source and a dose cup acoustically coupled to receive ultrasonic energy from the source. A domed element is removably disposed over the dose cup, establishing a substantially closed mist chamber-defining element therein. An inhalation port extends from the domed element, permitting a user to inhale the contents of the mist chamber-defining element. The conventional practice of nebulizing an aqueous solution in ultrasonic (or jet) nebulizers, involves a first step of removing the domed element (permitting user access to the dose cup), followed by breaking an ampoule or vial containing the medicament, and introducing the contents into a dose cup or chamber. The domed element is then replaced, and the ultrasonic energy source is activated, whereby the ultrasonic energy is transmitted to the dose cup, where it nebulizes the medicament. A user may then inhale via the inhalation port, as desired.

The method of introducing the medicament to the dose cup involves prolonged handling of the medicament by the patient and therefore may lead to hygiene issues and volume loss due to spillage or incomplete emptying of the ampoule. A further issue is the number of components which require cleaning following nebulization—dose cup, domed element, inhalation ports of the inhalation port, for example.

It is an object of this invention to provide an improved nebulizer apparatus and method which minimizes spillage of drug and the number of components to be cleaned.

Another object is to provide an improved nebulizer. Most conventional nebulizers allow free flow of air through a dose chamber during nebulization, which results in the exhalation of the patient forcing nebulized mist back into the dose chamber and device during exhalation. As a consequence, a large proportion of the dose condenses on the inside of the device and is therefore not delivered to the lung. It is another object of this invention to provide more efficient air control during inhalation and particularly exhalation, to significantly improve nebulizer performance.

SUMMARY OF THE INVENTION

The present invention provides a medicament delivery system. The medicament delivery system comprises a nebulizer, an open-faced mist chamber-defining element, coupling means for selectively coupling the coupling end of the mist chamber-defining element to the energy delivery end of the housing, a tubular inhalation port extending between a user end and a device end, and a bidirectional valve assembly.

In a preferred form of the invention, the nebulizer includes a housing extending along a housing axis from a base end to an energy delivery end. The housing includes an ultrasonic transducer responsive to applied electrical energy to generate ultrasonic energy at an output surface, and an ultrasonic transmission horn extending along the housing axis between an input energy surface and an output end. The input energy surface is acoustically coupled to the output surface of the transducer. The horn is adapted to transmit ultrasonic energy applied at the input energy surface along the housing axis to the energy delivery surface.

The open-faced mist chamber-defining element (which includes transparent, translucent and opaque elements) extends along a chamber axis from an open-faced coupling end. The mist chamber-defining element includes a tubular input/output port extending along a port axis, with the port axis being angularly offset from the chamber axis e.g., by an angle in the range of 35–55 degrees, such as 45 degrees. The chamber-defining element is selectively couplable to the energy delivery end of the housing so that the interior volume of the mist chamber is opposite the energy delivery surface of the horn and the chamber axis is substantially parallel to the housing axis. Preferably, the chamber-defining element is dome-shaped, so that when its open face is coupled to the housing, it defines the substantially closed mist chamber.

The bidirectional valve assembly has a first port coupled to the device end of the inhalation port, a second port coupled to the port of the mist chamber-defining element and a third port coupled to (which, in some embodiments, may be integral with) points exterior to the bidirectional valve assembly. The valve assembly defines a unidirectional airflow path only from the interior volume of the mist chamber to the user end of the inhalation port when the pneumatic pressure in the inhalation port is lower than the pneumatic pressure in the interior volume of the mist chamber. The valve assembly also defines a unidirectional airflow path only from the user end of the inhalation port to the exterior points when the pneumatic pressure in the inhalation port is greater than the pneumatic pressure in the interior volume of the mist chamber.

The medicament delivery system further includes a cup-shaped medicament ampoule having a removable (for example, by peeling off a foil cover) seal adapted to fit within the mist chamber-defining element. The ampoule has an open-faced interior region defined by a base member. The interior region extends from an open top ring at a top end along an ampoule axis to a closed end opposite the top end, wherein the closed end has an outer surface complementary to the energy delivery surface of the ultrasonic transmission horn. The ampoule is adapted to fit within the mist chamber-defining element with the outer surface of the closed end of the ampoule fitting in intimate contact with the energy delivery surface of the ultrasonic transmission horn. The ampoule further includes a medicament disposed in the interior region of the ampoule and wherein the open top ring of the ampoule is spanned by a sheet member whereby the interior region of the ampoule is closed.

The sealed unit dose ampoule (filled with the relevant medicament) is positionable into the device (with its seal intact), and when the seal is removed, the ampoule acts as both a dose cup negating the need for a separate baffle. With that configuration, drug handling is limited, the likelihood of spillage of the medicament is reduced, and consequently a consistent dose can be delivered. In a preferred form, the ampoule is disposable, minimizing the number of components to be cleaned.

The ampoule of the present invention is preferably essentially a small, thin walled cup. In one preferred embodiment, the unit dose ampoule includes an upper screw thread portion, a location ring and a conical base. The upper screw thread portion is adapted to be screw connected with the open-faced end of the mist chamber-defining element. The location ring allows the ampoule to be positioned within the nebulizer device. The base is preferably conical shaped to allow the ultrasonic energy conducted from the ultrasonic system to be concentrated at the base of the ampoule. This design also enables fluid returning of activated medicament from the sides of the ampoule to the point at which all the ultrasonic energy is concentrated. The ampoule has a predetermined volume designed to contain a required dose of medicament.

The inhalation port includes an inhalation valve, a main chamber and an exhalation valve. During inhalation by a user, the inhalation valve opens to allow passage of aerosol mist into the main chamber of the inhalation port and subsequently into the patient. At the same time the exhalation valve remains closed. During exhalation, the exhalation valve becomes operational to allow the breath to pass out of the inhalation port without entering the mist chamber, at the same time the inhalation valve remains closed to prevent breathing back into the dose unit.

The present invention is applicable for both solutions and suspensions. Drug applications may include all nebulized formulations, particularly in the following therapeutic areas—Asthma, COPD, Cystic Fibrosis, infections of any type responsive to antibiotic treatment, and pain treatment of any type.

DETAILED DESCRIPTION OF THE INVENTION

Figure 1:
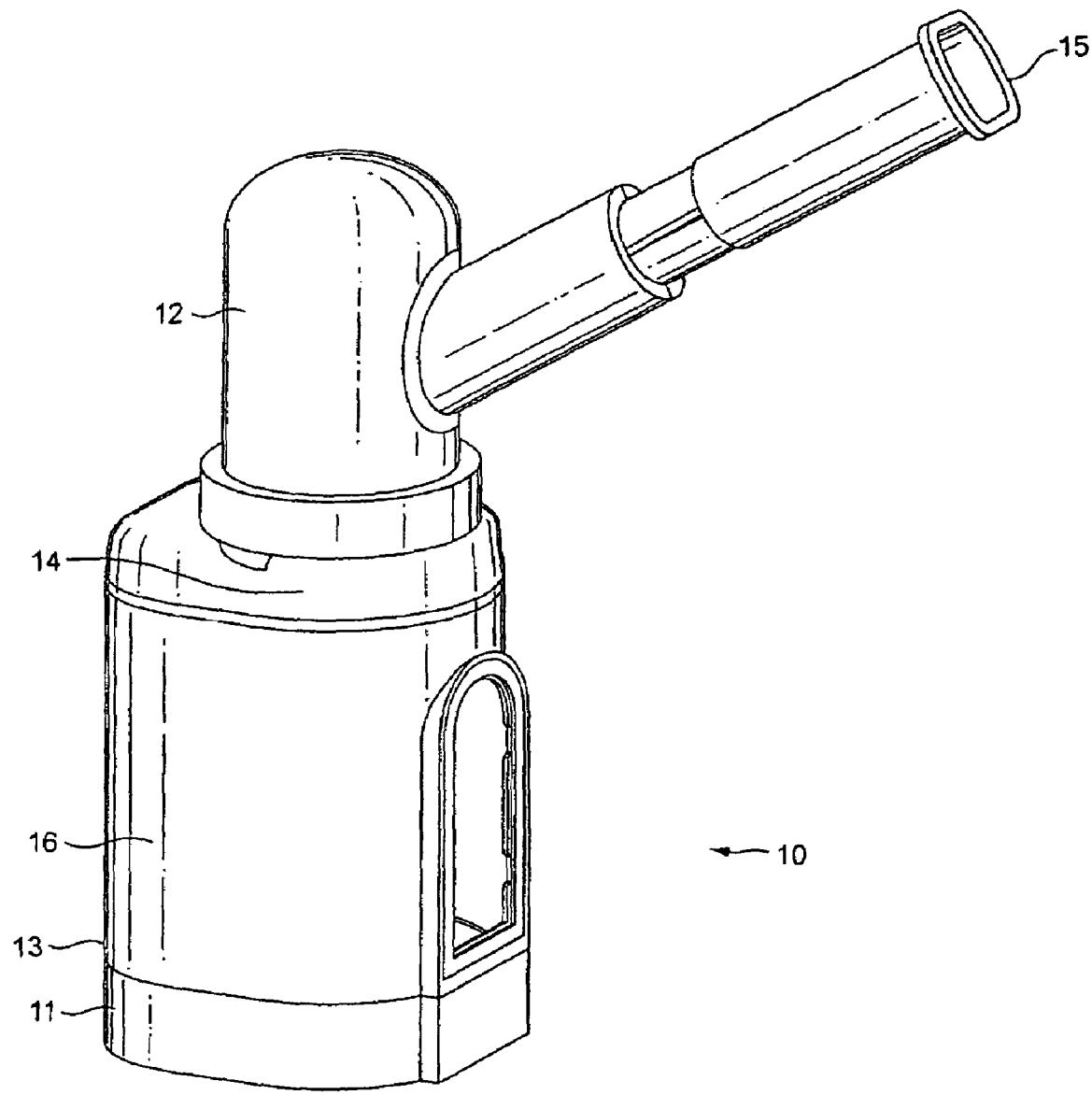
FIG. 1 is a perspective view of one embodiment of a nebulizer assembly in accordance with the invention.

For a better understanding of the invention, the following detailed description refers to the accompanying drawings, wherein preferred exemplary embodiments of the present invention are illustrated and described. In addition, the reference numbers used to identify like elements in the drawings are the same throughout.

The present invention, a medicament delivery system, comprises a nebulizer device, an open-faced mist chamber-defining element having a tubular input/output port, coupling means for selectively coupling the coupling end of the mist chamber-defining element to the energy delivery end of the nebulizer device, a tubular inhalation port extending between a user end and a device end, a bidirectional valve assembly, and a sealed unit dose ampoule adapted to fit within the mist chamber-defining element. The nebulizer device includes an ultrasonic transducer responsive to applied electrical energy to generate ultrasonic energy, an ultrasonic transmission horn between an input energy surface at an input end and an energy delivery surface at an output end. The sealed unit dose ampoule can be placed directly into the nebulizer device and acts as both the dose cup and baffle, so that the chance of spillage of drug and the number of components to be cleaned are minimized. The unit dose ampoule has a conical base to allow ultrasonic energy conducted from the ultrasonic system to be concentrated at the base of the ampoule. The inhalation port includes an inhalation valve and an exhalation valve.

Figure 2:
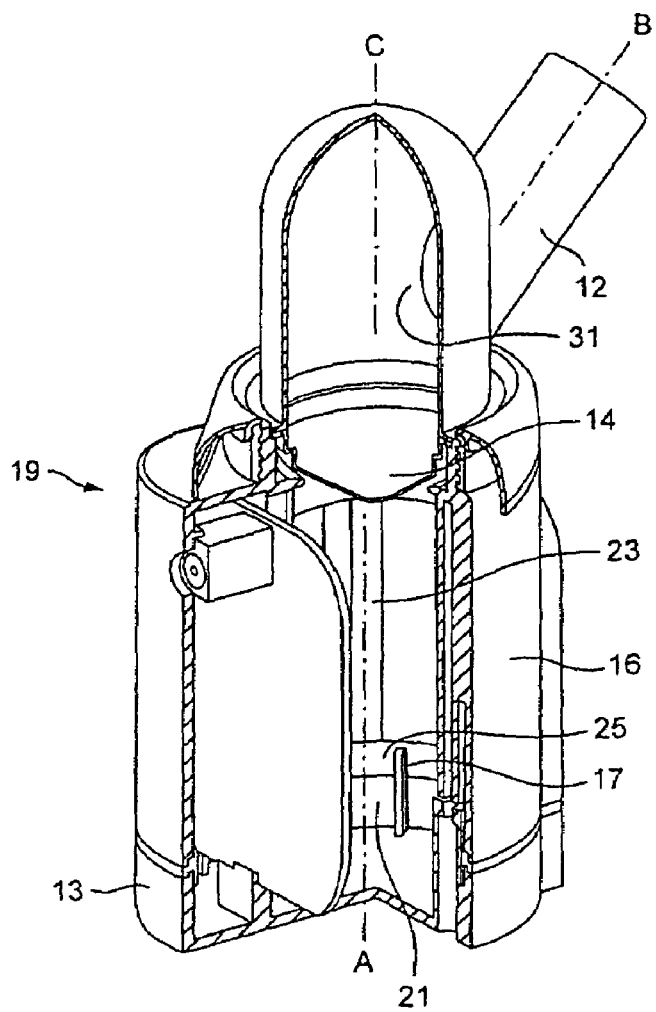
FIG. 2 is a perspective view of the nebulizer assembly of FIG. 1 partially cut-away to reveal internal components thereof.
Figure 3A:
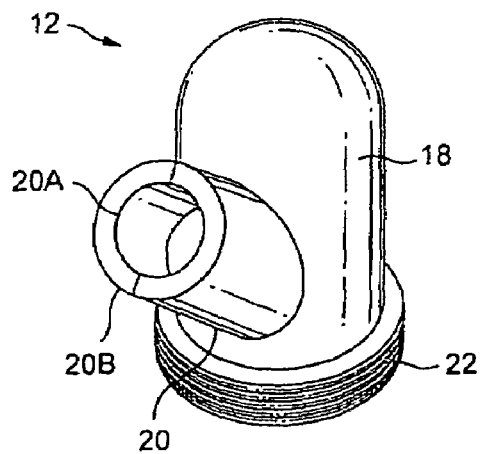
FIGS. 3A and 3B are perspective views of one embodiment of the mist chamber-defining element of the nebulizer assembly of FIG. 1.
Figure 3B:
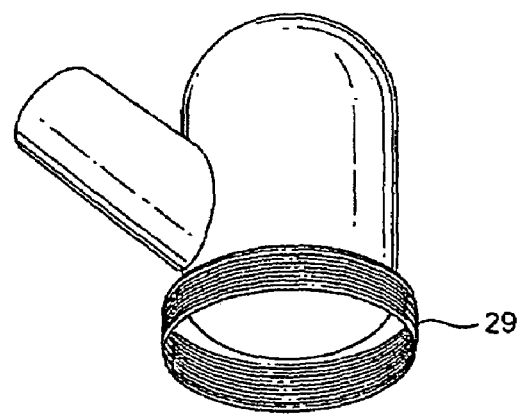
Figure 4:
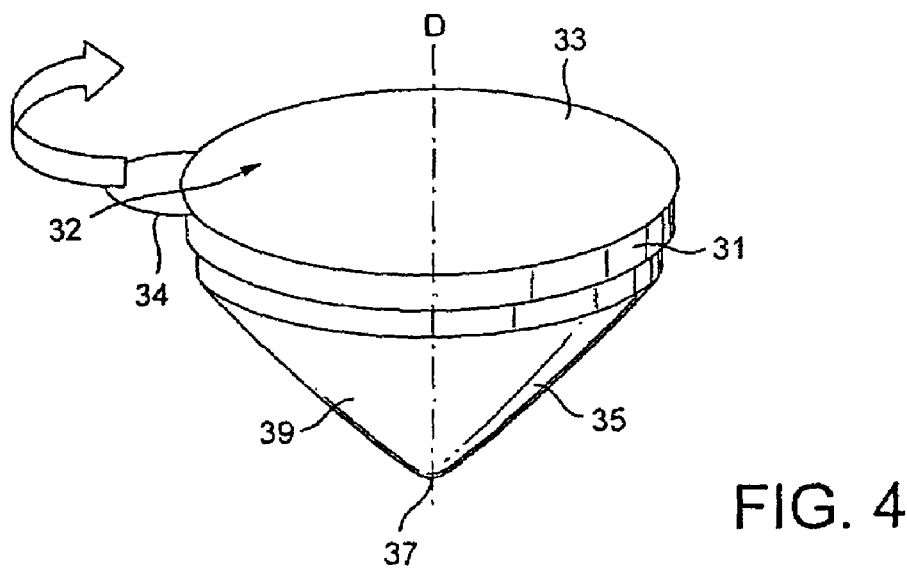
FIG. 4 is a perspective view of one embodiment of a unit dose ampoule for use with the nebulizer of FIG. 1, having a frangible seal.
Figure 4A:
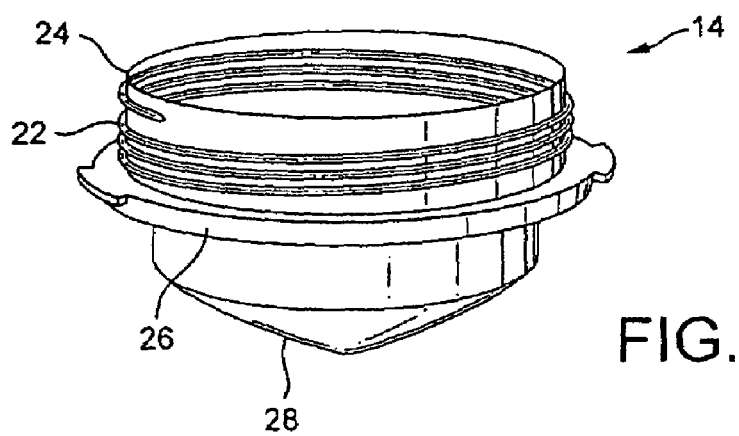
FIG. 4A is a perspective view of one embodiment of a unit dose ampoule for use with the nebulizer assembly of FIG. 1.
Figure 4B:
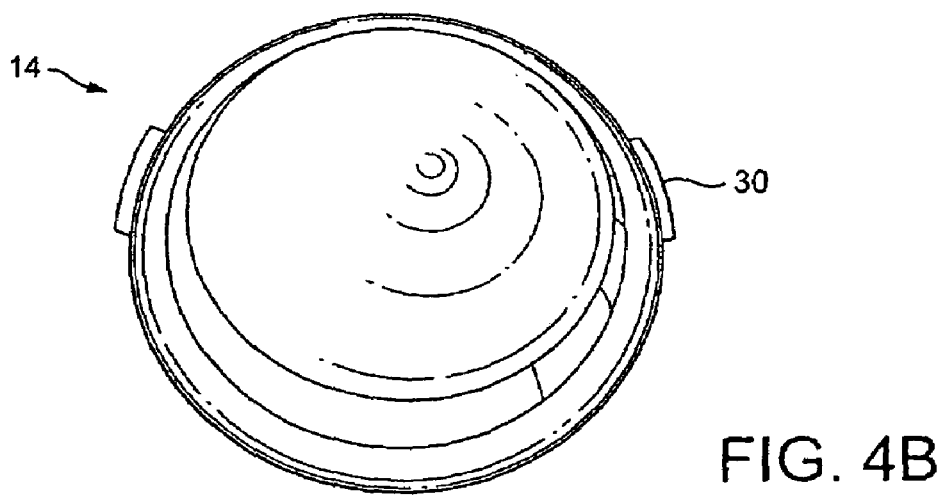
FIG. 4B is a bottom view of the unit dose ampoule of FIG. 4A.
Figure 5:
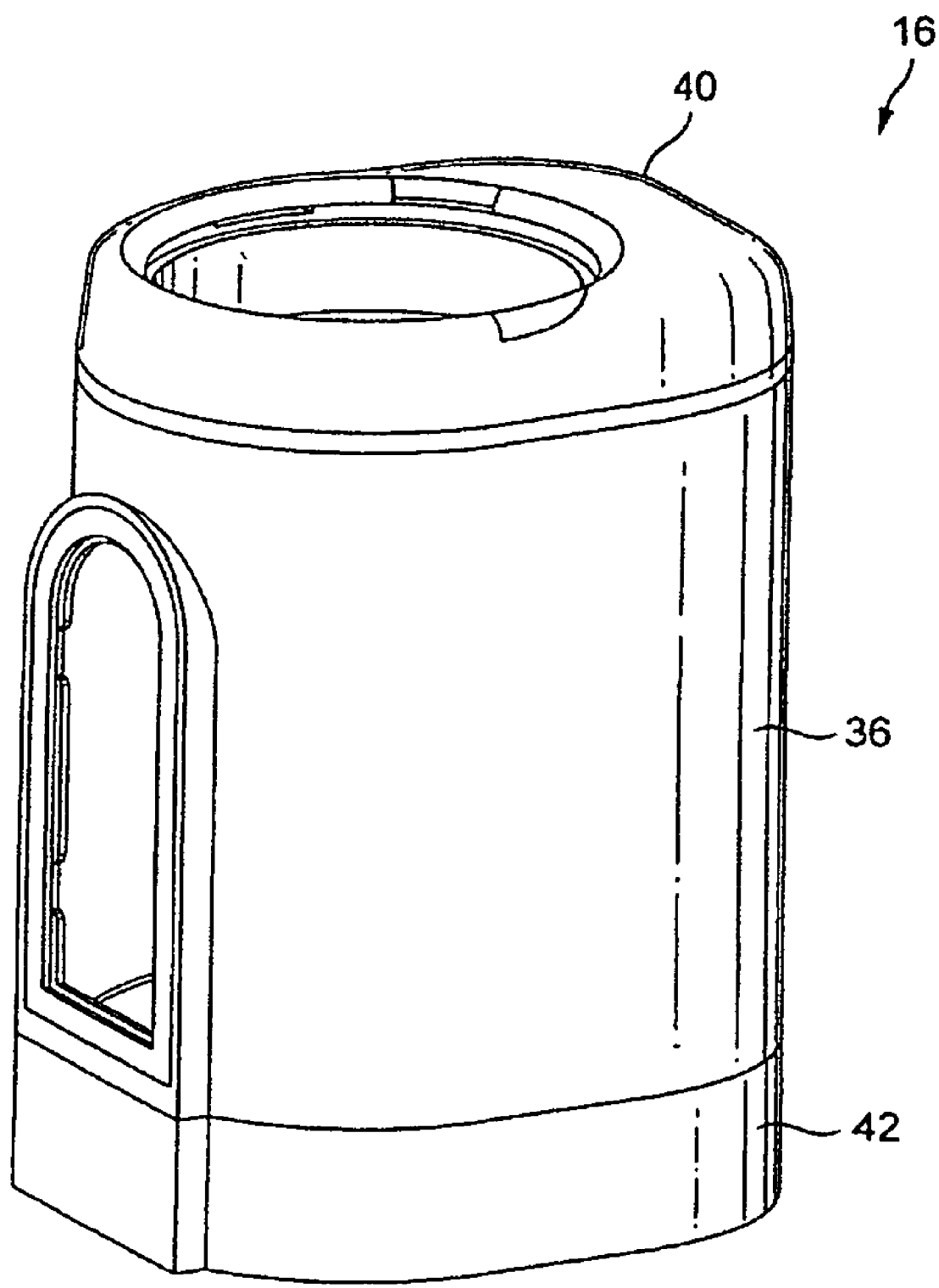
FIG. 5 is a perspective view of the nebulizer housing for the nebulizer assembly of FIG. 1.
Figure 5A:
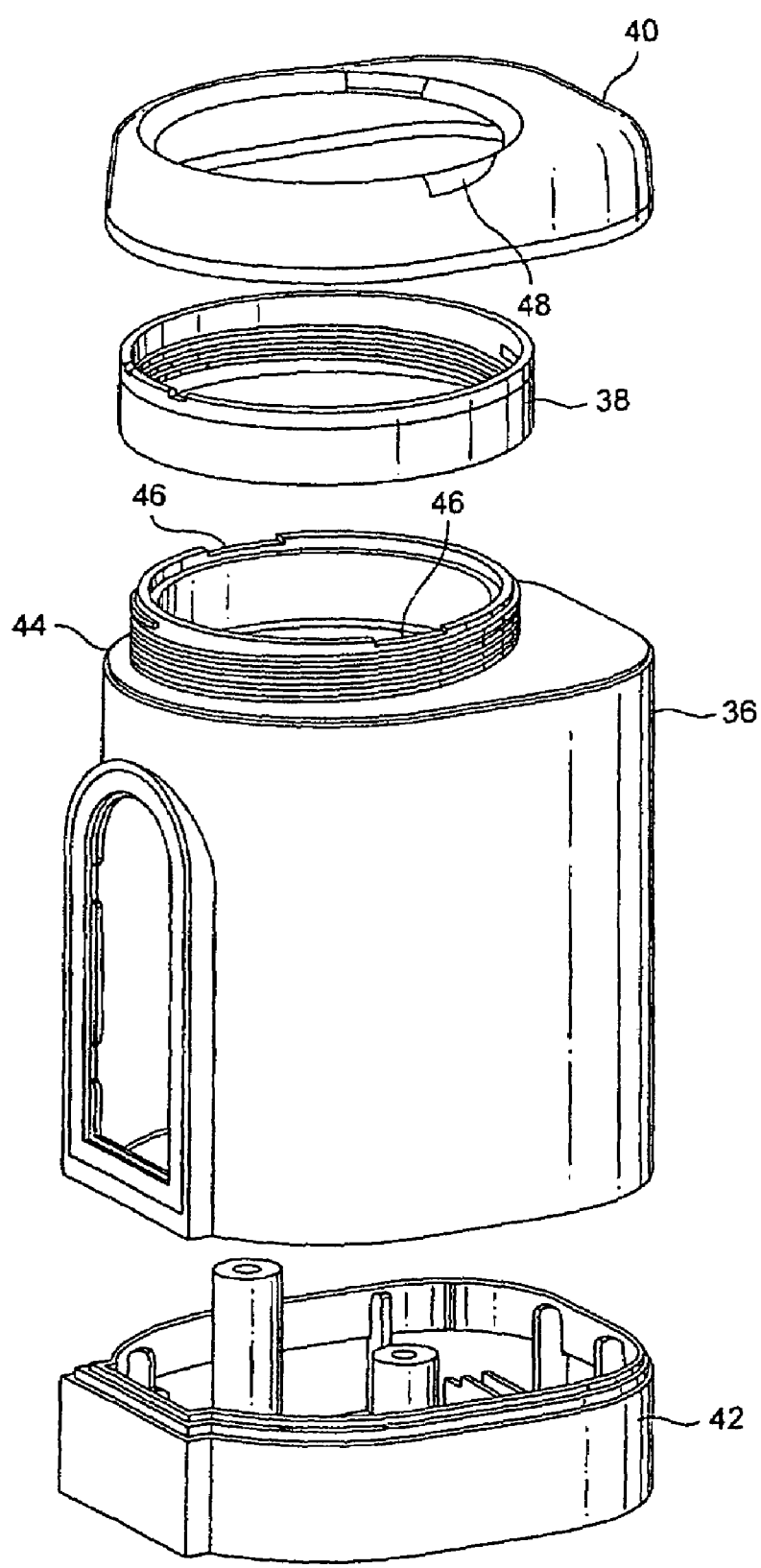
FIG. 5A is an exploded side view of the nebulizer assembly of FIG. 1.
Figure 6:
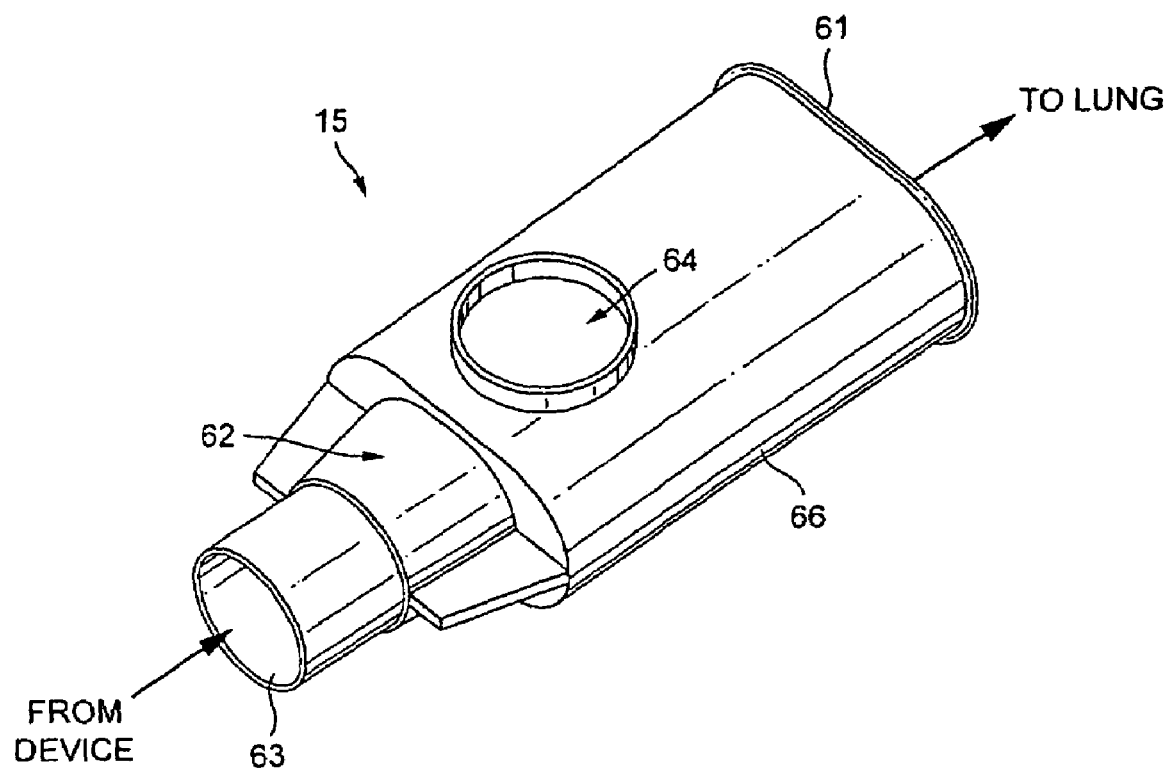
FIG. 6 is a perspective view of the inhalation port of the nebulizer assembly of FIG. 1.
Figure 6A:
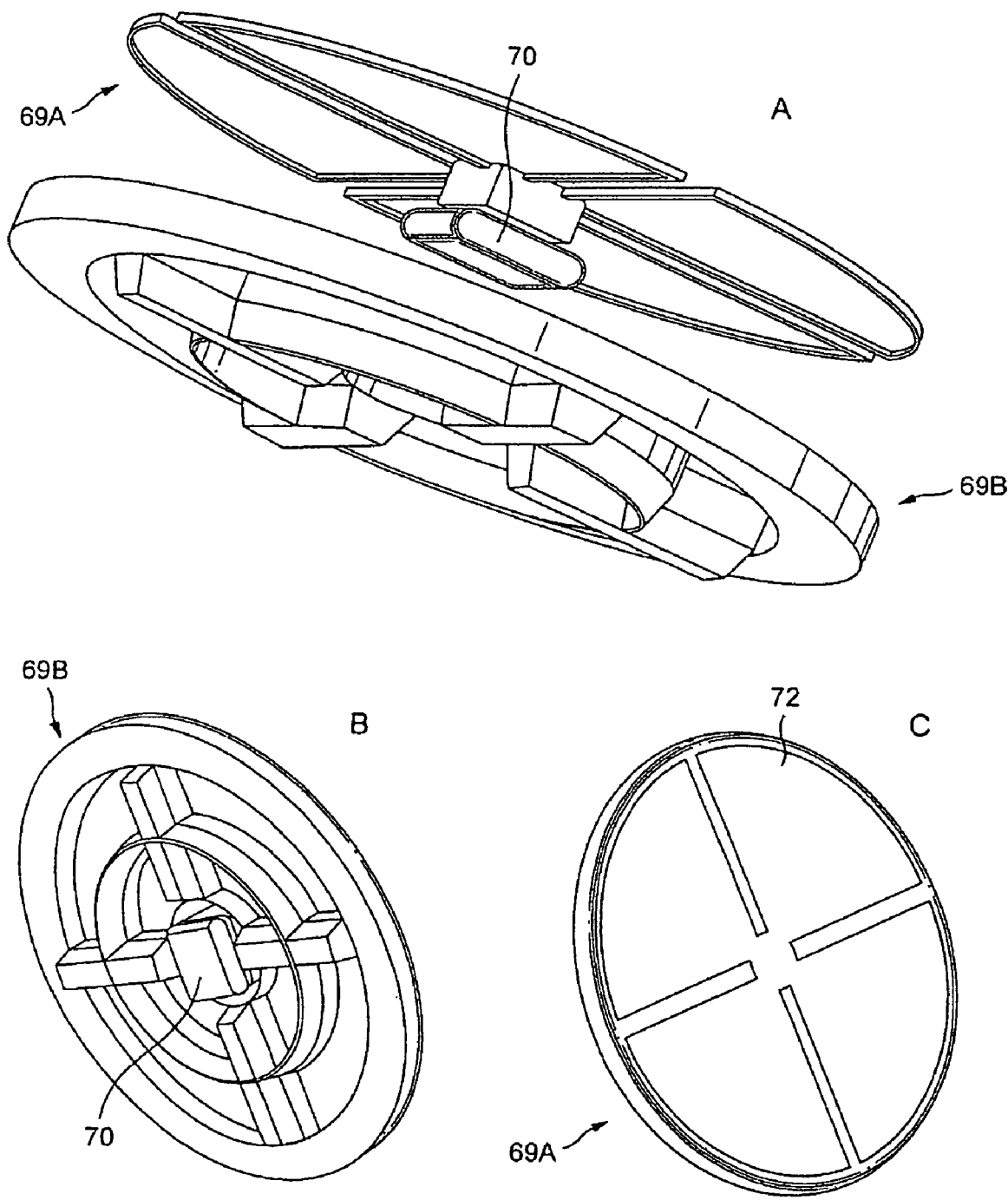
FIG. 6A illustrates one embodiment of the valve and retainer disc for use in the inhalation port of the nebulizer assembly of FIG. 1.
Figure 6B:
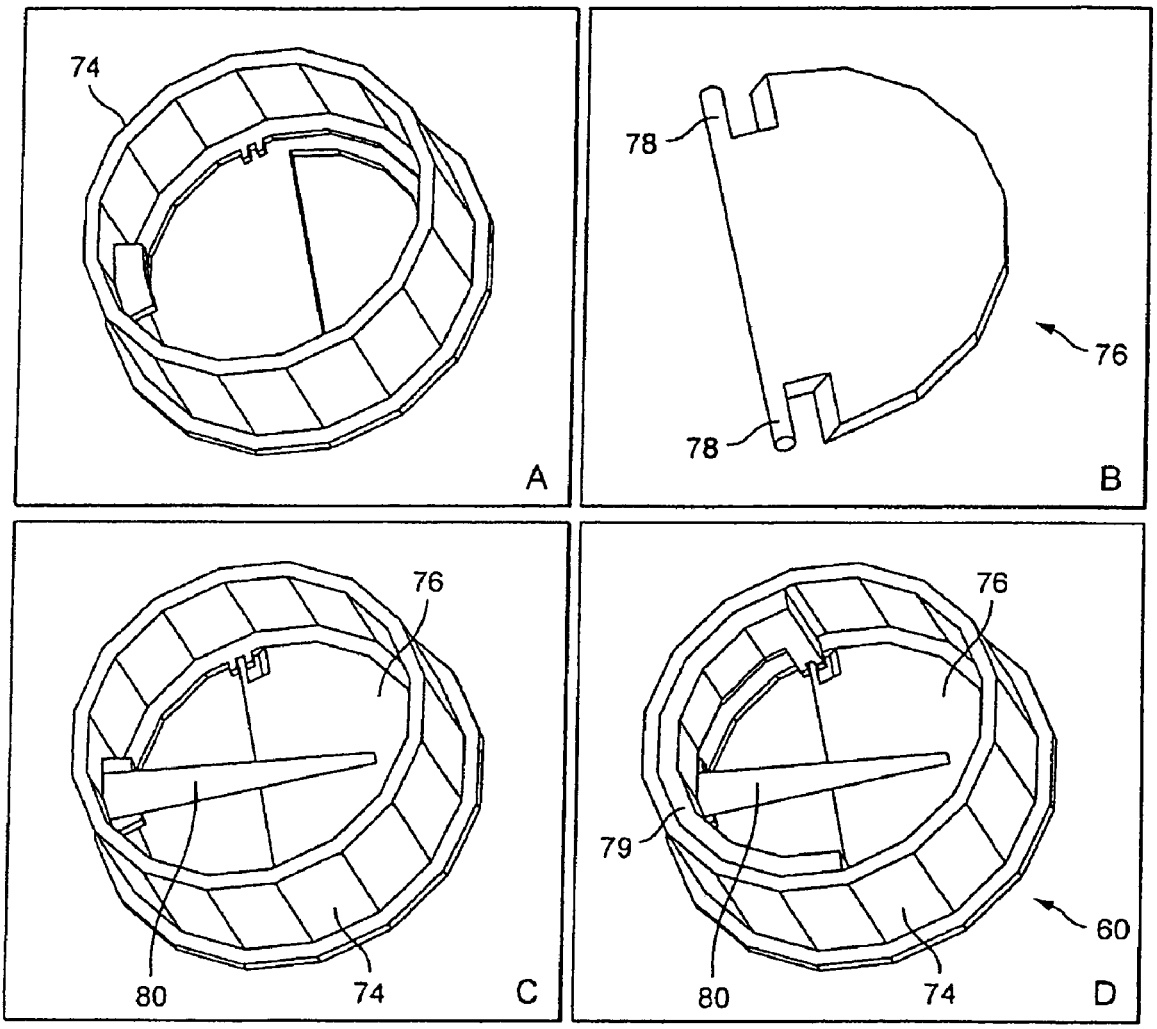
FIG. 6B illustrates another embodiment of the valve and retainer disc for use in the inhalation port of the nebulizer assembly of FIG. 1.

FIG. 1 and FIG. 2 illustrate an exemplary nebulizer assembly 10 embodying the present invention. As shown in FIGS. 1 and 2, the nebulizer 10 comprises a nebulizer 11, a mist chamber-defining element 12, an ampoule 14 for receiving medicament attached to the mist chamber-defining element 12, and a housing 16 enclosing an electrically driven ultrasonic system for generating ultrasonic energy and coupling that ultrasonic energy to the ampoule 14. The generally dome shaped mist chamber-defining element 12 together with the ampoule 14 defines a substantially closed mist chamber above the ampoule 14.

FIG. 2 is a perspective view of the nebulizer assembly of FIG. 1 partially cut-away to reveal internal components thereof. The nebulizer 11 includes a housing 16 extending along a housing axis A from a base end 13 to an energy delivery end 19. The housing 16 includes an ultrasonic transducer 21 responsive to applied electrical energy to generate ultrasonic energy at an output surface 17, and an ultrasonic transmission horn 23 extending along the housing axis A between an input energy surface 25 at an input end and an energy delivery surface 27 at an output end. The input energy surface 25 is acoustically coupled to the output surface 17 of the transducer. The horn 23 is adapted to transmit ultrasonic energy applied at the input energy surface 25 along the housing axis A to the energy delivery surface 27. The open-faced mist chamber-defining element 12 extending along a chamber axis C from the coupling end 29. The mist chamber-defining element 12 includes a tubular input/output port 31 extending along a port axis B, and the port axis B is angularly offset from the chamber axis C. The interior volume of the mist chamber-defining element 12 is opposite the energy delivery surface 27 of the horn 23 and the chamber axis C is substantially parallel to the housing axis A. Preferably, the chamber-defining element 12 is dome-shaped, so that when its open face is coupled to a perimeter of the ampoule 14, it defines the substantially closed mist chamber.

FIGS. 3A and 3B show a chamber-defining element of one preferred embodiment of the present invention. The chamber-defining element 12 includes a domed main chamber wall 18, an inhalation tube 20 in communication with the interior mist chamber defined by chamber wall 18, and a lower screw thread portion 22 extending from the main chamber wall 18 to the coupling end 29 of the chamber-defining element 12. The chamber wall 18 has vertical walls and a domed roof, the highest point of which being located at the center of the chamber cross-section and being, but not limited to, a hemispherical shape. The roof and chamber defined by chamber wall 18 are preferably smooth to allow condensed mist to run back down to be nebulized again to ensure efficient delivery of a high percentage of the dose. Other geometries of mist chamber may be used to create the same effect.

The inhalation port assembly formed by inhalation tube 20 is made up of two concentric tubes 20A and 20B. In the illustrated embodiment, the cross-sectional areas of the inner and outer tubes are the same to equilibrate the flow of air into and out of the chamber. Other geometries may be used in different forms of the invention. The inhalation tube 20 preferably connects to the wall 18 near the bottom of the mist chamber-defining element to avoid drawing in of medicament with a liquid form.

As shown in FIG. 4, FIG. 4A and FIG. 4B, the ampoule 14 has an open-faced interior region defined by a base member 35. The interior region is extending from an open top ring 31 at a top end 33 along an ampoule axis D to a closed end 37 opposite the top end 33, wherein the closed end 37 has an outer surface 39 complementary to the energy delivery surface 27 of the ultrasonic transmission horn 23. The ampoule 14 is adapted to fit within the mist chamber-defining element 12 with the outer surface 39 of the closed end 37 of the ampoule 14 fitting in intimate contact with the energy delivery surface 27 of the ultrasonic transmission horn 23.

As shown in FIG. 4, The ampoule 14 may further include a medicament disposed in the interior region of the ampoule and wherein the open top ring 31 of the ampoule is spanned by a sheet member 32 whereby the interior region of the ampoule is closed. The frangible sealed sheet member 32 across the top may be removed by tearing, piercing or breaking. In a preferred embodiment, the frangible seal member 32 is a foil or plastic lid, which is sealed to the ampoule 14 by ultrasonic weld or glue. The foil membrane has a side tab 34, or centralized semi-circular attachment to aid removal of the seal. The lid 32 is preferably not removed until the ampoule 14 is locked into the nebulizer. This design prevents spillage of the medication and reduces patient handling of the ampoule and the medicament. The lid 32 is preferably made from materials with low heat conductivity, low surface tension (to prevent coagulation of particles), and ease of manufacture.

As shown in FIG. 4A, the ampoule 14 of the present invention is essentially a small, thin walled cup having a conical base, to allow the ultrasonic energy conducted from the ultrasonic system to be concentrated at the base of the ampoule. In one preferred embodiment, the unit dose ampoule 14 includes an upper screw thread portion 24, a location ring 26, and a conical base 28. The screw thread of the upper screw thread portion 24 has equal pitch and length to the screw thread of the lower screw thread portion 22 of the chamber-defining element 12 to allow attachment of the ampoule 14 to the mist chamber-defining element 12 to form a complete unit. The fixture between mist chamber-defining element 12 and ampoule 14 is not limited to a screw thread. A snap/push fit or interference fit may be employed. The base 28 is preferably conical shaped to allow the ultrasonic energy to concentrate at the base of the ampoule. The conical shaped base also enables nebulized or activated medicament to run down the sides of the ampoule 14 to a bottom point at which all the ultrasonic energy is concentrated. The location ring 26 allows the ampoule 14 to be received and positioned at the top of the housing 16. The ring is preferably circular, but circumstances may require a triangular, rectangular, hex or pentagonal design adapted for using with different designed housings or ultrasonic systems. As best shown in FIG. 4B, two tabs 30 extend from the location ring 26. These tabs act to lock the ampoule 14 in the housing 16. The tabs are preferably spaced at an angle not equal to 180 degrees to ensure that the ampoule may only be oriented in one direction. In one preferred embodiment, an angle of 120 degrees has been chosen. The number of side tabs may not be limited to two. Also other means for coupling the chamber-defining element, the ampoule and the housing (and its ultrasonic generator) may be used.

In a preferred embodiment, as shown in FIG. 5 and FIG. 5A, the housing 16 of the present invention includes a main casing 36, a threaded collar 38, a cover 40, and a base 42. The top of the main casing 36 includes a threaded cylindrical section 44 with two cutout sections 46 to accommodate the two tabs 30 of the ampoule 14. The threaded collar 38 is screw mounted onto the threaded cylindrical section 44 of the main casing 36. The cover 40 is rotatably mounted onto the threaded collar 38, preferably snap-fitted to the collar 38. In one preferred embodiment (not shown in the figures), the cover 40 has two angularly offset stop plates engaged with one stop plate of the housing 16, thus only limited movement of the cover relative to the housing is permitted. The cover 40 further includes two cutouts 48, which are adapted to receive the two tabs 30 of the ampoule 14. When the cover 40 is rotated to a first position, the two cutouts 48 are aligned with the two cutout sections 46 of the housing 16, and the ampoule may be placed into a conical recess of the housing 16 with the two tabs 30 fitting into the two cutouts 48 of the cover 40 and the two cutout sections 46 of the housing 16. When the cover is rotated to a second position, the ampoule tabs are retained in the two cutout sections 46 of the housing 16, and the ampoule 14 is locked into the housing 16. In operation, after the ampoule 14 is placed and locked in the housing 16 and the lid 32 is removed, the mist chamber-defining element 12 is then screwed onto the top of the ampoule. The screw thread of the mist chamber-defining element is preferably designed to begin in one place to ensure that the inhalation tube on the mist chamber-defining element is oriented towards the front of the nebulizer body.

The nebulizer of the present invention further comprises an ultrasonic transducer disposed within the housing 16. The ultrasonic transducer is selectively responsive to applied electrical energy to generate ultrasonic energy, which is coupled via a transmission horn from an output surface of the transducer to an energy delivery surface near the top of the housing 16. The energy delivery surface is adapted to be in intimate contact with the conical base 28 of the ampoule 14, so that said energy transfer occurs. The delivered energy causes nebulization of the medicament.

Thus, the ultrasonic energy passes from the ultrasonic transducer, through the conical base of the unit dose ampoule 14 and into the aqueous medicament. This energy creates a fountain of liquid inside the ampoule and the mist chamber, and enables molecules with enough energy to break away from the fountain, creating the aerosol mist. This mist then is inhaled by a patient to the lungs of the patient.

As shown in FIG. 6, the inhalation port 15 extends between a user end 61 and a device end 63. Inhalation port 15 includes a bidirectional valve assembly made of two unidirectional valves. One valve is an inhalation valve 62, and the other one is an exhalation valve 64. During inhalation, the inhalation valve 62 opens to allow passage of the aerosol mist into a main chamber 66 of the inhalation port 15 and subsequently into the patient's lungs. At the same time the exhalation valve 64 remains closed. The exhalation valve 64 positioned in the side tube section becomes operational during exhalation to allow the breath to pass out of the inhalation port without entering the mist chamber, at the same time the inhalation valve 62 remains closed to prevent breathing back into the mist chamber.

The preferred embodiments of the inhalation and exhalation valves each includes a small, thin, rubber disc element 69A that is mounted to cover radial holes in a frame element 69B that allows the passage of air. In FIG. 6A, part A shows an exploded view of the valve, and parts B and C show front and rear views respectively. The disc element 69A includes a stem 70 in the center and a four segment thin rubber disc 72. During inhalation or exhalation, the peripheral portions of the thin rubber disc lift away from the frame element 69B, allowing the inhaled mist to pass into the inhalation port, or the exhaled breath into the air.

FIG. 6B shows another preferred embodiment of the valves. As shown in FIG. 6B, the valve has a valve housing 74 and a thin semicircular disc segment 76 with a pair of pins 78 extending therefrom. The disc segment 76 is pivotally connected to the valve housing 74 by the pins 78 and a retaining ring 79. A spring 80 biases the disc 76 toward a closed position. During inhalation or exhalation, the disc segment 76 lifts away from the housing 74, allowing the inhaled mist to pass into the inhalation port, or the exhaled breath into the air. During the opposite portion of the breathing cycle, the spring 80 forces the valve to be closed.

The bidirectional valve assembly, and the inhalation port 15 generally, define a unidirectional airflow path only from the interior volume of the mist chamber to the user end 61 of the inhalation port 15 when the pneumatic pressure in the inhalation port 15 is lower than the pneumatic pressure in the interior volume of the mist chamber. The valve assembly 60 also defines a unidirectional airflow path only from the user end of the inhalation port to the exterior points when the pneumatic pressure in the inhalation port is greater than the pneumatic pressure in the interior volume of the mist chamber.

The discs in both embodiments of FIG. 6A and FIG. 6B may only be lifted in one direction, so that the valves are remained close when the air breath comes from an opposite direction.

There are no restrictions on dimensions with the exception that the internal dimensions allow insertion of the inhalation and exhalation valves, and the inhalation port can be attached to the inhalation tube of the mist chamber-defining element.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

What is claimed is:

1. A medicament delivery system comprising:

A. a nebulizer including a housing extending along a housing axis from a base end to an energy delivery end, said housing including therein:

i. an ultrasonic transducer responsive to applied electrical energy to generate ultrasonic energy at an output surface thereof;

ii. an ultrasonic transmission horn extending along said housing axis between an input energy surface at an input end and an energy delivery surface at an output end, said input energy surface being acoustically coupled to said output surface of said transducer, said horn being adapted to transmit ultrasonic energy applied at said input energy surface along said housing axis to said energy delivery surface, B. an open-faced mist chamber-defining element extending along a chamber axis from an open-faced coupling end and said mist chamber-defining element including a tubular input/output port extending therefrom along a port axis, said port axis being angularly offset from said chamber axis, C. coupling means for selectively coupling said open-faced coupling end of said mist chamber-defining element to said energy delivery end of said housing whereby said interior volume of said mist chamber-defining element is opposite said energy delivery surface of said horn and said chamber axis is substantially parallel to said housing axis, D. a tubular inhalation port extending between a user end and a device end, E. a bidirectional valve assembly having a first port coupled to said device end of said inhalation port, a second port coupled to said port of said mist chamber-defining element and a third port coupled to points exterior to said bidirectional valve assembly, wherein said valve assembly defines a unidirectional airflow path only from said interior volume of said mist chamber-defining element to said user end of said inhalation port when the pneumatic pressure in said inhalation port is lower than the pneumatic pressure in said interior volume of said mist chamber-defining element, and wherein said valve assembly defines a unidirectional airflow path only from said user end of said inhalation port to said exterior points, when the pneumatic pressure in said inhalation port is greater than the pneumatic pressure in said interior volume of said mist chamber-defining element.

2. A medicament delivery system according to claim 1, further comprising:

a cup-shaped medicament ampoule having an open-faced interior region defined by a base member extending from an open top ring at a top end along an ampoule axis to a closed end opposite said top end, wherein said closed end has an outer surface complimentary to said energy delivery surface of said ultrasonic transmission horn, and wherein said ampoule is adapted to fit within said mist chamber-defining element with said outer surface of said closed end of said ampoule fitting in intimate contact with said energy delivery surface of said ultrasonic transmission horn.

3. A medicament delivery system according to claim 1 wherein said ampoule includes a medicament disposed in said interior region of said ampoule and wherein said open top ring of said ampoule is spanned by a sheet member whereby said interior region of said ampoule is closed.

4. A medicament delivery system according to claim 3 wherein said sheet member is removable.

5. A medicament delivery system according to claim 3 wherein said sheet member is frangible.

6. A medicament delivery system according to claim 1 wherein aid mist chamber-defining element is dome-shaped.

7. A medicament delivery system according to claim 1 wherein said port axis is offset from said chamber axis by an angle in the range 35 to 55 degrees.

8. A medicament delivery system according to claim 1 wherein said port axis is offset from said chamber axis by 45 degrees.

9. A medicament delivery system according to claim 1 wherein said energy delivery surface is cone-shaped.

10. A medicament delivery system according to claim 1 wherein said bi-directional valve assembly is a discrete assembly adapted for removable coupling of said second port of said bi-direction valve assembly.

11. A medicament delivery system according to claim 1 wherein said bi-directional valve assembly is integral with said port of said mist chamber-defining element.

12. A medicament delivery system according to claim 1 wherein said mist chamber-defining element is transparent.

13. A medicament delivery system according to claim 1 wherein said mist chamber-defining element is translucent.

14. A medicament delivery system according to claim 1 wherein said mist chamber-defining element is opaque.

* * * * *

UNITED STATES PATENT AND TRADEMARK OFFICE
CERTIFICATE OF CORRECTION

PATENT NO. : 7,261,102 B2
APPLICATION NO. : 10/487611
DATED : August 28, 2007
INVENTOR(S) : Brian Barney et al.

Page 1 of 1

It is certified that error appears in the above-identified patent and that said Letters Patent is hereby corrected as shown below:

Column 1, line 56, "minimizes" should read --minimize--
Column 1, line 56, after "of" insert --the--
Column 4, line 32, after "of" insert --the--
Column 4, line 64, "extending" should read --extends--
Column 5, line 45, "The" should read --the--
Column 6, line 10, "conical shaped" should read --conical-shaped--
Column 7, line 23, "includes" should read --include--
Column 7, line 57, "close" should read --closed--
Column 9, line 9, "aid" should read --said--
Column 9, line 12, after "range" insert --of--.

Signed and Sealed this

Eighth Day of July, 2008

JON W. DUDAS
*Director of the United States Patent and Trademark Office*